United States Patent [19]
Gallub

[11] 4,183,353
[45] Jan. 15, 1980

[54] METHOD AND POSITION MARKER FOR THE DETECTION OF DEEP VEIN THROMBOSIS

[75] Inventor: Thomas M. Gallub, Walton, Ky.

[73] Assignee: Actus, Inc., Florence, Ky.

[21] Appl. No.: 919,218

[22] Filed: Jun. 26, 1978

[51] Int. Cl.² .............................................. A61B 6/00
[52] U.S. Cl. .................................. 128/654; 101/405; 128/659; 128/661
[58] Field of Search .............. 128/2 A, 2 B, 2 R, 2 V, 128/316; 118/264; 101/405

[56] References Cited
U.S. PATENT DOCUMENTS

| | | | |
|---|---|---|---|
| 3,502,070 | 3/1970 | Bliss | 128/2 B |
| 4,030,414 | 6/1977 | McGuire | 101/405 X |
| 4,092,980 | 6/1978 | Frank et al. | 128/2 A |

Primary Examiner—Kyle L. Howell
Attorney, Agent, or Firm—Fleit & Jacobson

[57] ABSTRACT

Disclosed is a position marker in the form of a crescent ink stamp or the like for use in conjunction with a detector apparatus for detecting deep vein thrombosis. When in use, the position marker prints a series of overlapping circles. The diameters of the overlapping circles substantially correspond to the diameter of the detector probe, and the amount of overlap is related to the effective area of the probe's crystal sensor.

6 Claims, 10 Drawing Figures

METHOD AND POSITION MARKER FOR THE DETECTION OF DEEP VEIN THROMBOSIS

BACKGROUND OF THE INVENTION

There are several devices on the market today which are designed for the early detection of deep vein thrombosis. The devices include hand-held detector probes sensitive to radiation, and electronics to convert the detected radiation to meaningful data. Typically, such devices are operated in the leg region.

In this procedure, an I-125 labeled fibrinogen is intravenously injected into the patent. Then, the leg is marked with a map to guide the operator in sequentially positioning the detector probe. Once the injected fibrinogen tracer has dispersed throughout the body (in the neighborhood of three hours), radiation readings are taken with the deep vein thrombosis detection apparatus. First, a precordial count is made, and the, with the markings previously positioned on the leg, radiation counts are made along the leg, generally as a percent of the precordial count, and the readings are plotted. Localized excesses of the radioactive fibrinogen tracer are indicative of dot formations.

While the procedures for detecting deep vein thrombosis have proven valuable, sensitivity is lost because of the relatively crude techniques employed for positioning the detector probe on the area of interest. That is, by drawing spaced-apart lines on the leg, and then positioning the probe between successive lines during a counting and plotting operation, areas of the leg between markings are not scanned. This is basically because the outside diameter of the detector probe is greater than the effective diameter of the detector crystal itself.

It is toward increasing the sensitivity of deep vein thrombosis detection that the present invention is directed.

SUMMARY OF THE INVENTION

The present invention relates generally to the field of deep vein thrombosis detection, and more specifically, to a position marker in the form of an ink stamp or the like, for developing maps to ensure the most effective positioning of the detector probe during the scanning procedure. Specifically, the inventive position marker provides an ink stamp having the format of a crescent having a principal circle whose diameter is slightly greater than the outside diameter of the detector probe, and an intersecting circle of the same diameter. In use, the position marker developes successive ink traces which form a pattern of overlapping circles, so that when the detector probe is positioned at each location, it is ensured that the crystal sensor takes a reading at every region in the area of interest.

It is accordingly a principal object of the present invention to provide a position marker for use in the field of deep vein thrombosis detection, for enhancing the efficiency of thrombosis detection.

A more specific object of the present invention is to provide a position marker in the form of an ink stamp or the like which insures that the crystal sensor of a thrombosis detector is positioned over every region of interest during a detection procedure.

A further object of the present invention is to provide a position marker having an efficacious format and guide marks to facilitate the development of a complete mapping pattern.

Still another object of the present invention is to provide a crescent-format position marker for developing an overlapping-circle mapping pattern.

A further object of the present invention is to provide an efficient method of carrying out the procedure of deep vein thrombosis detection.

These and other objects of the present invention, as well as many of the attendant advantages thereof, will become more readily apparent when reference is made to the following description, taken in conjunction with the accompanying drawings.

DETAILED DESCRIPTION OF THE DRAWINGS

Figure 1:
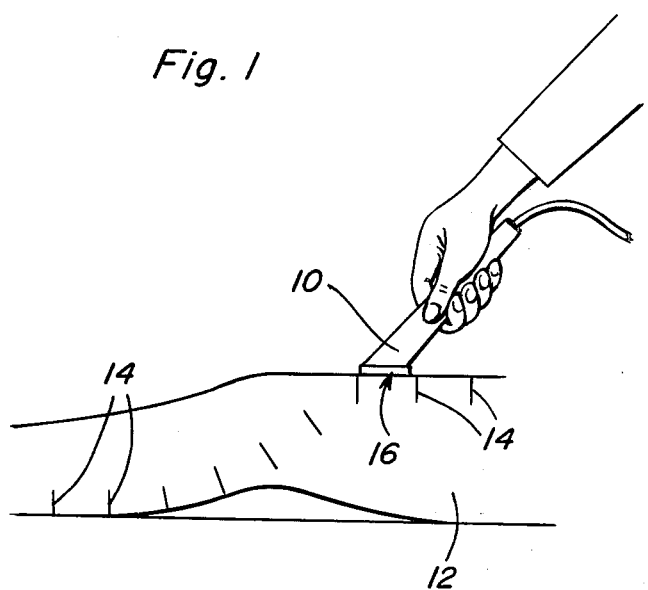
FIG. 1 is an illustration showing a prior art thrombosis detection procedure.

With reference first to FIG. 1, the known technique of deep vein thrombosis detection will be described. Initially, the patient is injected with a fibrinogen labeled with a radioactive material such as I-125. The labeled fibrinogen is then allowed to distribute itself through the circulatory system for somewhere in the neighborhood of three hours, and then the detection procedure can be initiated. A detector probe, illustrated at 10 in FIG. 1, is designed to detect the presence of radioactive material in the circulatory system. Specifically, the detector probe includes a photoluminescent detector crystal which emits flashes of light each time it is bombarded by a radioactive particle. Suitable electronics are provided in the detector apparatus (not shown) fed by the probe 10 for providing a count, or readout of detected radioactivity.

Figure 1A:
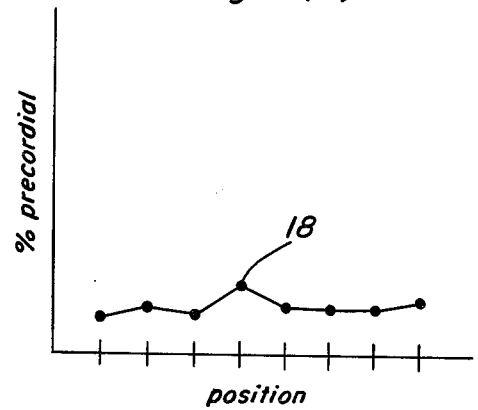
FIG. 1(a) is a tracing illustrating the results of the procedure shown in FIG. 1.

Preliminary to the commencement of a detection procedure, the region of interest, in this case the leg, shown at 12, is marked by guide marks 14 forming a mapping pattern. As can be seen, marks 14 are spaced apart by a distance slightly greater than the diameter of the head 16 of detector probe 10. In this manner, the operator merely follows the pattern of markings 14, takes a reading at each location defined between markings 14, and continues this procedure until the number of readings indicated by the mapping pattern are completed. Before taking the first reading on the leg, a precordial count is taken, and the "baseline" is set by the precordial reading. That is, the radioactive fibrinogen detected at predetermined locations on the leg are measured directly as a percentage of the precordial count. A typical tracing can be seen in FIG. 1(a), with the position of a potential deep vein clot being indicated at 18.

Figure 2:
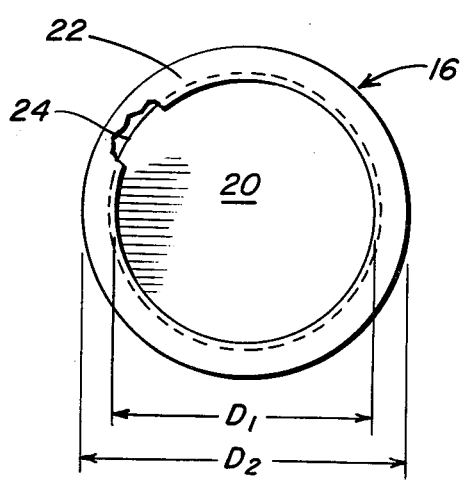
FIG. 2 illustrates the face of a typical detector probe.
Figure 3:
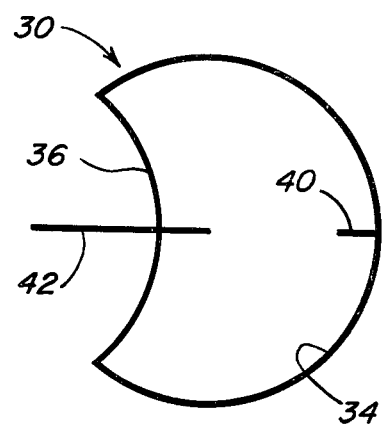
FIG. 3 is an illustration of the inventive position marker format.

FIG. 2 illustrates the head 16 of a typical detector probe 10. A photoluminescent detector crystal 20 is positioned in a central location in the head, and is held in place by means of a cap, or retainer ring 22. The crystal 20, as noted above, is designed to count radioactive particles, by emitting flashes of light each time it is bombarded by a particle. These light flashes are then optically coupled, appropriately amplified, and ultimately read out of the detector instrument (not shown) as a percentage, number of counts, or some other indication of the radiation detected.

As can be seen in FIG. 2, the crystal 20 is slightly larger in diameter than the inside diameter $D_1$ of the retainer ring 22; the outside diameter of crystal 20 is indicated at 24. Still, however, the effective diameter of crystal 20 is diameter $D_1$, the inside diameter of the retainer ring 22, since the radioactive particles are not able to penetrate the retainer ring 22. Accordingly, while the outside diameter $D_2$ of probe head 16 is larger than inside diameter $D_1$ of retainer ring 22, crystal 20 is capable only of effectively receiving radiation from the area immediately beneath the retainer ring 22 and defined by diameter $D_1$. It can be seen, therefore, with reference to FIG. 1, that there is a region of leg 12 not scanned by the prior art deep vein detection techniques. This is the case even if markings 14 were spaced apart by precisely the diameter of head 16.

With reference, then, to FIGS. 3 through 8, the inventive position marker will be described. The position marker is indicated generally at 30, and takes the form of an ink stamp or the like mounted on an appropriate holder shown at 32 in FIGS. 7 and 8. In use, the operator holds the position marker by its holder 32, applies the same to a stamp pad, and then marks the leg with a mapping pattern, all as will be described below.

Figure 5:
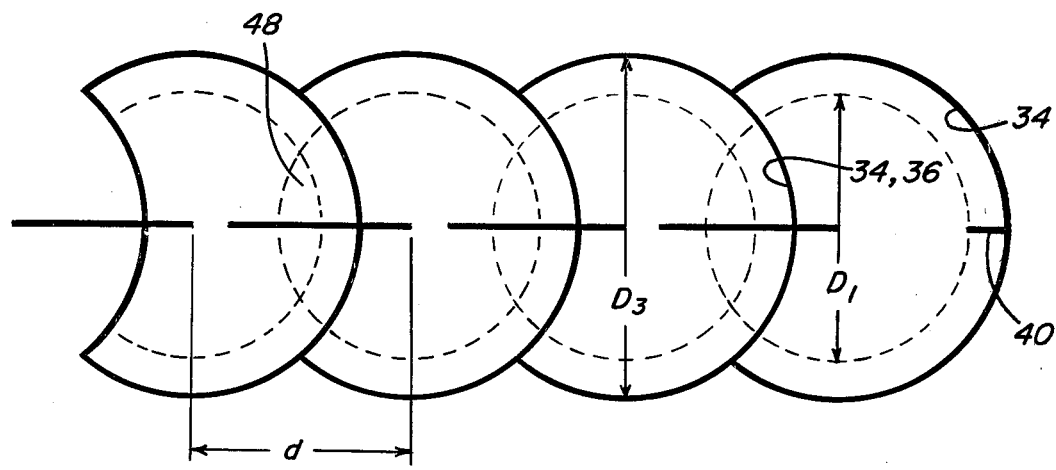
FIG. 5 is an illustration of a mapping pattern obtained by successive markings from the inventive position marker.

The format of position marker 30 is crescent defined by a first circle 34 having a diameter $D_3$ which is slightly larger than the outside diameter $D_2$ of detector probe head 16, and a second overlapping circle 36 of the same diameter $D_3$. As can be seen in FIG. 5, the amount of overlap is determined by the spacing d between the centers of circles 34 and 36. For purposes of the present invention, the spacing d is made equal to or less than $D_1$, the inside diameter of retaining ring 22.

Figure 4:
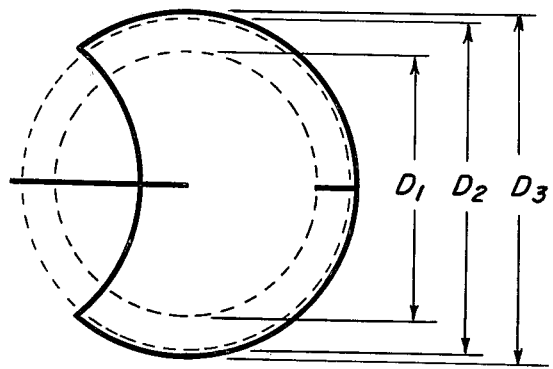
FIG. 4 is an illustration similar to FIG. 3, but showing the cooperation between the detector probe and the position marker.

FIG. 4 illustrates the relationship between diameter $D_3$ of overlapping circles 34 and 35, outside diameter $D_2$ of retaining ring 22, and inside diameter $D_1$ of retaining ring 22. Dotted circles representing inside diameter $D_1$, or the effective area of crystal 20, are carried over into FIG. 5. In this regard, it will be noted that the mapping pattern set forth in FIG. 5 is developed by successive markings of the position marker 30; the rear portion of each position marker stamping, including the section defined by circle 36, is overlapped by the next successive stamping, but at the section defined by circle 34.

To enable the operator to easily develop a mapping pattern, position marker 30 is provided with guide marks. A small guide mark 40 is provided at the front of position marker 30 lying on the common diameters of circles 34 and 36, lies inside and just touches circle 34. A larger rear guide mark 42 is located on the same diameter as is guide mark 40, and extends rearwardly from the center of circle 34, intersects circle 36, and is of a length designed to overlap the mark 40 made by the preceding position marker stamp.

Figure 6:
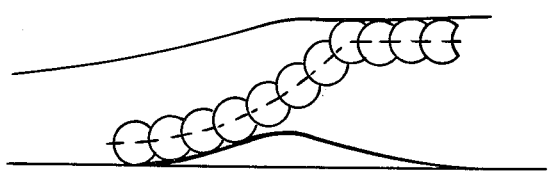
FIG. 6 is an illustration similar to FIG. 1, but showing the inventive position marker in use.
Figure 7:
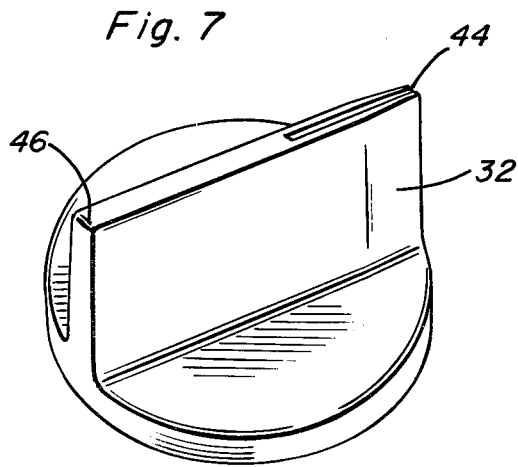
FIG. 7 is a top perspective view of the position marker complete with holder.
Figure 8:
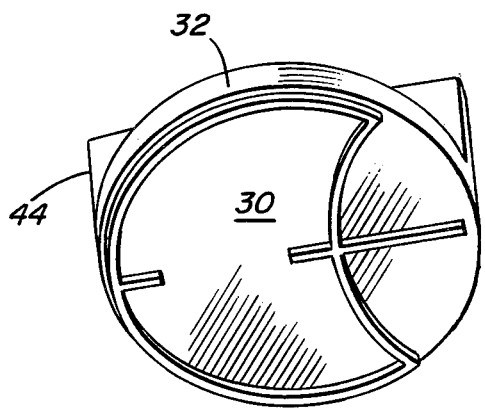
FIG. 8 is a bottom perspective view of the position marker and holder illustrated in FIG. 7.

The hand held portion illustrated in FIGS. 7 and 8 also has an indication to denote the direction of the stamp. In this regard, it can be seen that an arrow-shaped grip is provided, with the front of the arrow indicated at 44, and the rear of the arrow indicated at 46. Arrow front 44 denotes the location of mark 40. In this way, the operator is able to stamp the leg, as shown in FIG. 6, ensuring that the position marker 30 is always aligned in the proper direction.

In FIG. 5, it can be seen that the dotted circles representing the inside diameter $D_1$ of retaining ring 22 are slightly overlapped in regions 48. This will occur when the spacing d between the centers of circles 34 and 36 is less than the inside diameter $D_1$ of retaining ring 22. If $d=D_1$, on the other hand, there will be no overlap, but a tangential relationship will exist between the dotted circles illustrated in FIG. 5.

Figure 6A:
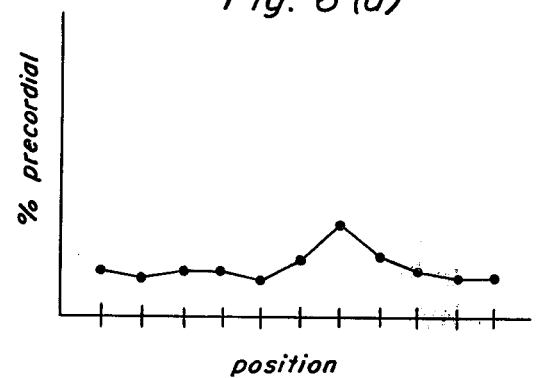
FIG. 6(a) is a tracing similar to that shown in FIG. 1(a), but related to the procedure illustrated in FIG. 6.

In practical effect, the spacing between centers of circles 34 and 36 of position marker 30 determines the tangential or overlapping relationship between the effective area of detector crystal 20 at successive thrombosis detection readings. It is contemplated by the present invention that d be equal to or less than $D_1$, thus ensuring at least a tangential relationship. In this manner, the detector crystal 20 is made to reside at all locations along the continuous scanning route. Although this procedure will certainly involve more readings that are taken in the prior art, the efficiency of detection will be greater. Furthermore, by using the inventive marker, the quality, or accuracy of the sequential counts will be enhanced. This is illustrated in FIG. 6(a), a drawing similar to that shown in FIG. 1(a).

Above, a specific embodiment of the present invention has been described. It should be appreciated, however, that this embodiment was described for purposes of illustration only, and is in no way intended to limit the scope of the present invention. Rather, it is the intention that the present invention be limited only as defined in the appended claims.

What is claimed is:

1. A position marker for use in mapping a series of readings in a deep vein thrombosis detection scan by means of a detector having a probe containing a detector crystal with an effective detection area less than the area of the face of the probe head, the position marker comprising:

a substantially planar face having a marking pattern thereon for scribing markings on an area to be scanned;

said marking pattern being in the format of a crescent defined by a first circle having a diameter slightly greater than the outside diameter of the detector probe face, and an overlapping second circle intersecting said first circle, said second circle having a diameter equal to that of said first circle, and the spacing between centers of said first and second circles being equal to or less than the effective diameter of the detector crystal.

2. The position marker recited in claim 1, and further comprising guide marks on the common diameters of said first and second circles.

3. The position marker recited in claim 2, wherein there are two guide marks, one intersecting said second circle, and one terminating at the interior of said first circle.

4. The position marker recited in claim 1, and further comprising handle means to enable an operator to mark the scan area.

5. The position marker recited in claim 4, and further comprising indicator means on said handle means to indicate direction, and wherein said marking pattern is in alignment with said indicator means.

6. A method for the detection of deep vein thrombosis utilizing a detector having a probe head wherein a detector crystal has an effective detection diameter less than the diameter of the probe head, the method comprising the steps of:

placing successive markings mapping a scan pattern on the region to be scanned, each marking being in the format of a crescent defined by a first circle having a diameter slightly larger than the outside diameter of said probe head, and a second circle intersecting said first circle, said second circle being of a diameter equal to said first circle, and the distance between centers of said first and second circles being less than or equal to the effective diameter of the detector crystal; and placing siad probe head within successive markings, and detecting the presence of a previously injected radioactive tracer.

* * * * *